(12) United States Patent
Tanahashi

(10) Patent No.: US 8,668,637 B2
(45) Date of Patent: Mar. 11, 2014

(54) ENDOSCOPIC IMAGE PICKUP DEVICE

(75) Inventor: Fuminori Tanahashi, Hachioji (JP)

(73) Assignee: Olympus Medical Systems Corp. (JP)

( * ) Notice: Subject to any disclaimer, the term of this patent is extended or adjusted under 35 U.S.C. 154(b) by 1297 days.

(21) Appl. No.: 12/237,839

(22) Filed: Sep. 25, 2008

(65) Prior Publication Data
US 2009/0247825 A1 Oct. 1, 2009

(30) Foreign Application Priority Data

Mar. 27, 2008 (JP) .................. 2008-084535

(51) Int. Cl.
*A61B 1/00* (2006.01)
*A61B 1/04* (2006.01)

(52) U.S. Cl.
USPC ............ 600/112; 600/109; 600/118; 600/160

(58) Field of Classification Search
USPC .......... 600/118, 160, 104, 101, 109, 112, 110
See application file for complete search history.

(56) References Cited

U.S. PATENT DOCUMENTS

| | | | | |
|---|---|---|---|---|
| 4,248,213 A | * | 2/1981 | Landre | 600/174 |
| 4,866,516 A | | 9/1989 | Hibino et al. | |
| 4,905,082 A | * | 2/1990 | Nishigaki et al. | 348/73 |
| 4,998,282 A | * | 3/1991 | Shishido et al. | 381/77 |
| 5,159,446 A | * | 10/1992 | Hibino et al. | 348/65 |
| 5,307,804 A | * | 5/1994 | Bonnet | 600/109 |
| 5,785,644 A | * | 7/1998 | Grabover et al. | 600/131 |
| 6,390,972 B1 | * | 5/2002 | Speier et al. | 600/112 |
| 7,189,247 B1 | * | 3/2007 | Zirps et al. | 606/140 |
| 2002/0103418 A1 | | 8/2002 | Maeda et al. | |
| 2003/0021557 A1 | * | 1/2003 | Eichelberger et al. | 385/101 |
| 2004/0133075 A1 | | 7/2004 | Motoki et al. | |
| 2004/0171912 A1 | | 9/2004 | Shimizu | |

(Continued)

FOREIGN PATENT DOCUMENTS

| | | |
|---|---|---|
| JP | 01-211716 | 8/1989 |
| JP | 7-116113 | 5/1995 |

(Continued)

OTHER PUBLICATIONS

JP2000-227559 JP-English Machine Translation Hagiwara et al. Aug. 15, 2000.*

(Continued)

*Primary Examiner* — Anhtuan T Nguyen
*Assistant Examiner* — Arnaldo Torres Diaz
(74) *Attorney, Agent, or Firm* — Ostrolenk Faber LLP

(57) ABSTRACT

An endoscopic image pickup device includes a sheath functioning as insertion section which is inserted in a body cavity, a camera head body which is coupled to a proximal end portion of the sheath in a direction perpendicular to an axis of the sheath, is rotatable about the axis of the sheath as a rotational axis, and has a center of gravity below the rotational axis, and a remote control section which is provided at a position with an extension below the camera head body. With this structure, even if an endoscope is rotated about the axis of the sheath of the endoscope, the camera head body is always kept in a constant attitude by its own weight. In addition, blurring of an image can be prevented at a time of capturing a still image by the operation of the remote control section.

4 Claims, 5 Drawing Sheets

(56) References Cited

U.S. PATENT DOCUMENTS

| | | | |
|---|---|---|---|
| 2005/0049458 A1* | 3/2005 | Honda et al. | 600/118 |
| 2005/0197533 A1* | 9/2005 | May et al. | 600/164 |
| 2007/0060789 A1 | 3/2007 | Uchimura et al. | |
| 2007/0213590 A1* | 9/2007 | Squicciarini | 600/172 |
| 2008/0009672 A1* | 1/2008 | Krattiger et al. | 600/112 |
| 2011/0251459 A1* | 10/2011 | Ferreira et al. | 600/118 |

FOREIGN PATENT DOCUMENTS

| | | |
|---|---|---|
| JP | 8-15614 | 1/1996 |
| JP | 2000-227559 | 8/2000 |
| JP | 2000-300513 | 10/2000 |
| JP | 2000-333902 | 12/2000 |
| JP | 2001-17388 | 1/2001 |
| JP | 2002-360579 | 12/2002 |

OTHER PUBLICATIONS

Hitoshi, Kimura JP 2000-333902A English Machine Translation May 12, 2000.*

European Search Report dated Aug. 3, 2009 in corresponding European Patent Application No. EP 08 01 7005 (English language).

Letter from German associate dated Aug. 6, 2009 forwarding the European Search Report dated Aug. 3, 2009 to Japanese associate, including discussion of relevancy thereof. German associate's letter dated Aug. 6, 2009 was date stamped received by Japanese associate on Aug. 7, 2009 (English language).

Office Action issued by the Japanese Patent Office on Sep. 4, 2012 in connection with corresponding Japanese Patent Application No. 2008-084535.

Translation of the Office Action issued by the Japanese Patent Office on Sep. 4, 2012 in connection with corresponding Japanese Patent Application No. 2008-084535.

* cited by examiner

ENDOSCOPIC IMAGE PICKUP DEVICE

CROSS-REFERENCE TO RELATED APPLICATIONS

This application is based upon and claims the benefit of priority from prior Japanese Patent Application No. 2008-084535, filed Mar. 27, 2008, the entire contents of which are incorporated herein by reference.

BACKGROUND OF THE INVENTION

1. Field of the Invention

The present invention relates to an endoscopic image pickup device which is connected to a proximal end portion of an insertion section which is to be inserted into a body cavity, and includes a camera head which captures an image in the body cavity.

2. Description of the Related Art

As an endoscope for medical treatment, there is known an endoscope apparatus which is disclosed, for example, in Jpn. Pat. Appln. KOKAI Publication No. H8-15614 (Patent Document 1). In this apparatus, a hand switch is detachably attached to a grip section which is provided at a proximal end portion of an insertion section which is to be inserted in a body cavity. An operation button of the hand switch of the grip section is operated while the body cavity is being observed. Thereby, a control unit can be remote-controlled to control a light source device, a color monitor, a VTR, etc.

Jpn. Pat. Appln. KOKAI Publication No. H7-116113 (Patent Document 2), for instance, discloses an endoscope apparatus wherein a camera head is detachably attached to an eyepiece section of an endoscope via a camera adapter. In this case, a push switch is provided on the camera head. By operating the push switch, like the case of Patent Document 1, a control unit can be remote-controlled to control a light source device, a color monitor, a VTR, etc.

Jpn. Pat. Appln. KOKAI Publication No. 2001-17388 (Patent Document 3), for instance, discloses an endoscope apparatus having a different structure. In this apparatus, a camera head is provided in a direction which is perpendicular to the axial direction of the insertion section of the endoscope and is a vertical direction. The camera head is provided on the eyepiece section of the endoscope via an endoscope connection portion in such a manner as to be rotatable about the axis of the insertion section of the endoscope. In this Patent Document 3, the endoscope connection portion, which is fixed to the eyepiece section of the endoscope, and the camera head are coupled to be rotatable about the axis of the insertion section. Thus, at the time of operating the endoscope, when the insertion section is rotated about its axis, only the insertion section rotates and the camera head does not rotate. With this structure, the camera head is kept in the vertical attitude, and an erecting endoscopic image is displayed on a TV monitor.

Further, Jpn. Pat. Appln. KOKAI Publication No. 2000-227559 (Patent Document 4), for instance, discloses an endoscopic image pickup device wherein optical axis deflecting means, which is composed of a beam splitter or a triangular prism, is provided in a camera head in the structure of the endoscopic image pickup device of Patent Document 3. By this structure, even if the optical axis of the camera head is misaligned with the optical axis of the endoscope, an erecting endoscopic image is displayed on the TV monitor.

BRIEF SUMMARY OF THE INVENTION

According to an aspect of the present invention, there is provided an endoscopic image pickup device comprising: an insertion section which is inserted in a body cavity; a camera head body which is coupled to a proximal end portion of the insertion section in a direction perpendicular to an axis of the insertion section, is rotatable about the axis of the insertion section as a rotational axis, and has a center of gravity below the rotational axis; and a remote control section which is provided at a position with an extension below the camera head body.

Preferably, the camera head body has a camera head housing having a center line which is substantially perpendicular to the rotational axis, and the remote control section is provided at a position with an extension from a lower end portion of the camera head housing.

Preferably, a camera cable, which is connected to a camera control unit, is connected to a lower end portion of the camera head body, and the remote control section is provided at a point along the camera cable.

Preferably, a camera cable, which is connected to a camera control unit, is connected to a lower end portion of the camera head body, and the remote control section is provided on a control cable which is connected to the camera control unit, and the remote control section is detachably attached to a point along the camera cable.

Preferably, the remote control section is connected to a control cable which is led out from the camera head body.

Preferably, a camera cable, which is connected to a camera control unit and in which a video signal line and a switch operation signal line are inserted, is connected to a lower end portion of the camera head body, the camera cable is relayed via the remote control which includes switch means, and the video signal line penetrates the remote control section, and the switch operation signal line is connected to the switch means.

Preferably, a camera cable, which is connected to a camera control unit and in which a video signal line and a switch operation signal line are inserted, is connected to a lower end portion of the camera head body, and the video signal line is covered with a shield member which is provided in the remote control section.

Preferably, the camera cable is coated with a shield line, and the shield line is connected to the shield member of the remote control section.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
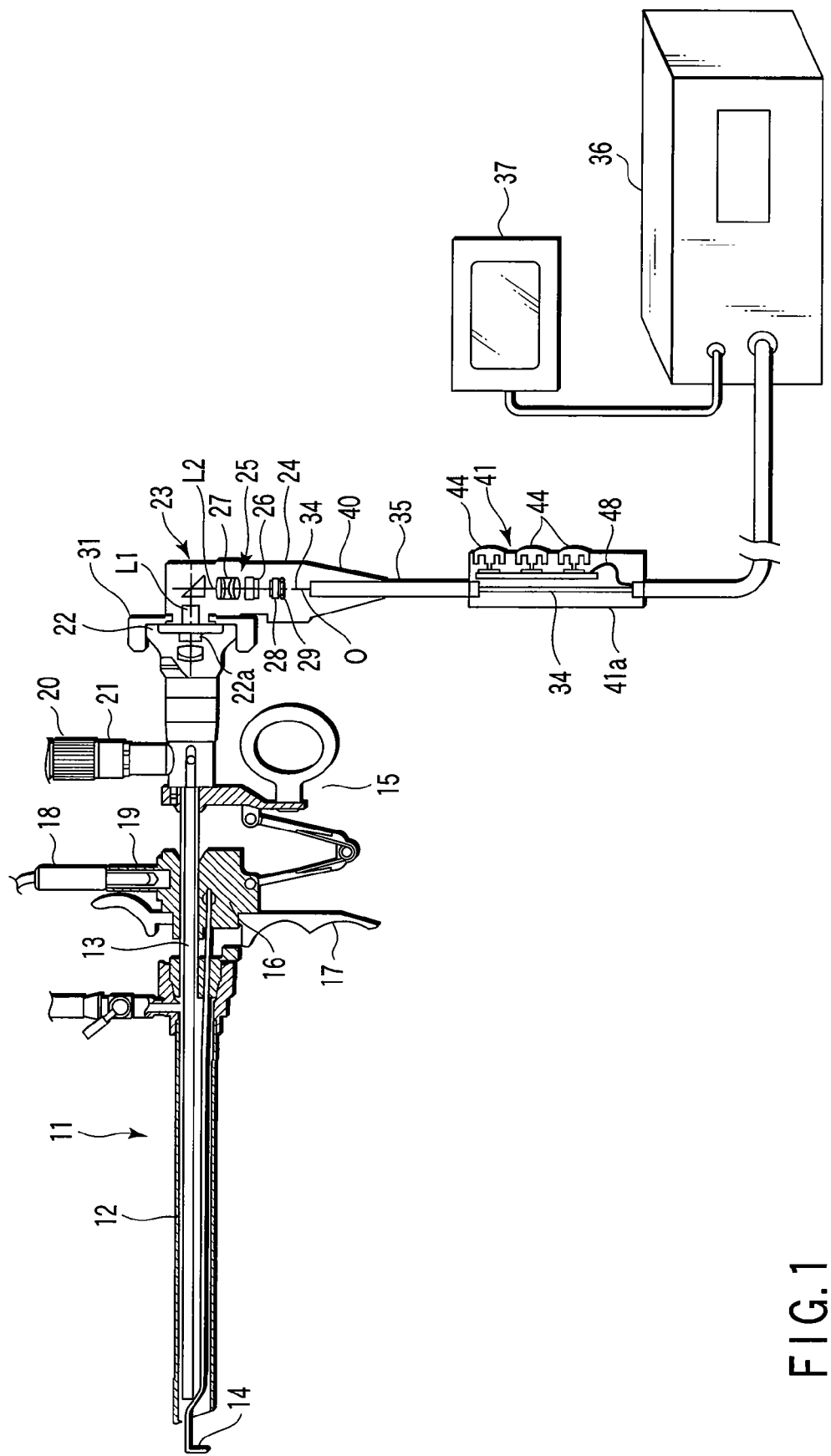
FIG. 1 shows the structure of an endoscopic image pickup device according to a first embodiment of the present invention.
Figure 2:
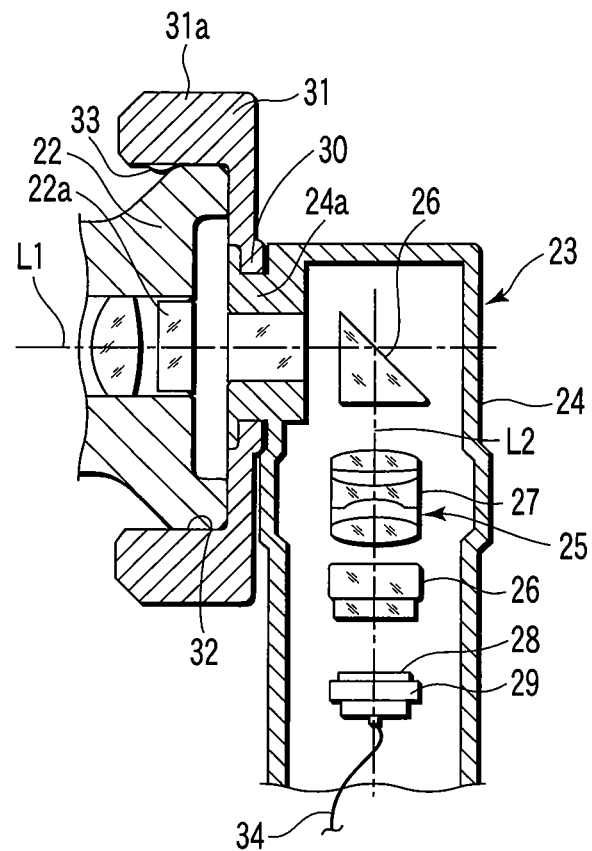
FIG. 2 is a longitudinal cross-sectional side view of a camera head body according to the first embodiment.
Figure 3A:
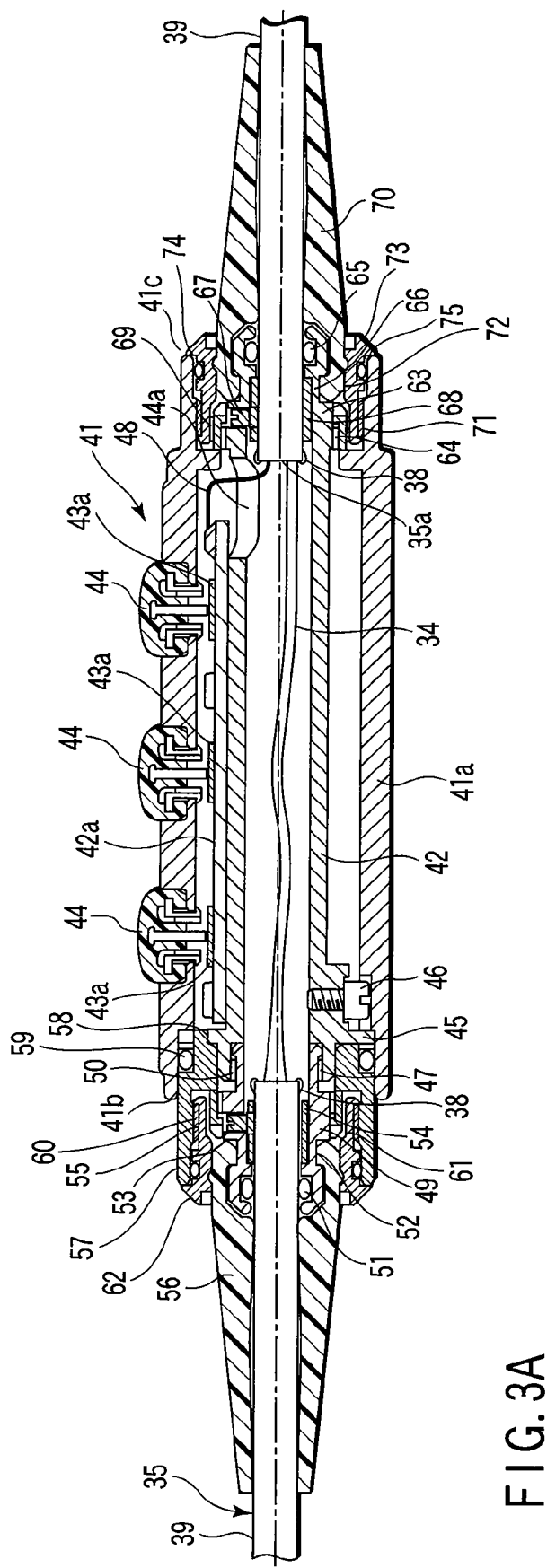
FIG. 3A is a longitudinal cross-sectional side view of a remote control section according to the first embodiment.

Embodiments of the present invention will now be described with reference to the accompanying drawings. FIG. 1 to FIG. 3B show a first embodiment of the invention. FIG. 1 shows the structure of an endoscopic image pickup device which is applied to a resectoscope. FIG. 2 is a longitudinal cross-sectional side view of a camera head body, and FIG. 3A is a longitudinal cross-sectional side view of a remote control section.

As is shown in FIG. 1, a resectoscope 11 functioning as a rigid endoscope includes a sheath 12 functioning as an insertion section which is to be inserted in a body cavity. In the sheath 12, a distal-end-side portion of a telescope 13 and a distal-end-side portion of a resecto-electrode member 14 are inserted and disposed in parallel. A grip handle 15 is provided at a proximal end portion of the sheath 12. The resecto-electrode member 14 is coupled to a slide operation member 16 which is provided on the proximal end portion of the sheath 12.

The slide operation member 16 is provided with a finger hooking operation handle 17 for an advancing/retreating operation. A user performs an operation of advancing/retreating the slide operation member 16 in the axial direction of the sheath 12 by hooking the fingers on the finger hooking operation handle 17 and grip handle 15. Thereby, the resecto-electrode member 14 is advanced/retreated in the axial direction of the sheath 12, and a therapeutic treatment of cutting a living body tissue by a high-frequency current is performed. A power connector 19 is provided on an upper end portion of the slide operation member 16. A high-frequency power cable 18, which leads to a high-frequency power supply (not shown), is connected to the power connector 19.

A light source connector 21 is projectingly provided on an outer peripheral surface of a proximal end portion of the telescope 13. A light guide cable 20, which extends from an illumination light source device (not shown), is connected to the light source connector 21.

An eyepiece section 22, which includes an eyepiece lens 22a, is provided at the proximal end portion of the telescope 13. The eyepiece section 22 is formed in a taper shape with a diameter gradually increasing rearward. A camera head body 23, which will be described below, is detachably attached to the eyepiece section 22.

The camera head body 23 comprises a camera head housing 24 and an image pickup optical system 25. The image pickup optical system 25 is housed in the camera head housing 24. The camera head housing 24 is formed in a substantially circular cylindrical shape. The image pickup optical system 25 includes prisms 26 functioning as optical axis deflecting means, a focusing optical system 27 comprising a plurality of lenses, a filter 28, and an image pickup element 29 such as a CCD.

A circular cylindrical projecting portion 24a is provided on a side surface of an upper end portion of the camera head housing 24. An annular groove 30 is provided in an outer peripheral surface of the projecting portion 24a. A mount member 31 for mounting the camera head body 23 on the eyepiece section 22 is rotatably engaged with the annular groove 30.

The mount member 31 includes an annular mount member body 31a. A mounting hole 32 for engagement with the eyepiece section 22 is provided on a distal-end surface side of the mount member body 31a. A camera coupling hole 31b having a smaller diameter than the mount hole 32 is formed in a rear end portion of the mount member body 31a.

A peripheral portion of the camera coupling hole 31b of the mount member 31 is rotatably engaged with the annular groove 30 of the camera head housing 24. Specifically, a small gap is provided in the annular groove 30 at an engaging connection part for engagement with the amount member 31. Thereby, the annular groove 30 and the mount member 31 are coupled such that their engagement connection part may smoothly rotate. Therefore, free rotation of the camera head body 23 is enabled, relative to the mount member 31.

An engaging projection 33 for engagement with an outer peripheral portion of the eyepiece section 22 is formed on an inner peripheral surface of the mounting hole 32 of the mount member 31. When the eyepiece section 22 is inserted and engaged in the mounting hole 32 of the mount member 31, the engaging projection 33 on the inner peripheral surface of the mounting hole 32 engages the outer peripheral portion of the eyepiece section 22. Accordingly, the camera head 23 is rotatable, relative to the eyepiece section 22 of the telescope 13, via the mount member 31 about the axis of the telescope 13, that is, about an optical axis L1.

Further, the prism 26 in the camera head body 23 is disposed on the optical axis L1. An optical axis L2 of the image pickup optical system 25 is perpendicular to the optical axis L1 of the telescope 13. Specifically, in FIG. 2, the optical axis L2 of the image pickup optical system 25 vertically extends at a central part of the camera head body 23. The prism 26, which is positioned at the uppermost part, the focusing optical system 27, the filter 28 and the image pickup element 29 are successively arranged, in the named order, in the downward direction on the optical axis L2. Thus, the center of gravity, O, of the camera head body 23 is positioned below the optical axis L1 of the telescope 13 (i.e. the rotational axis of the camera head body 23). With this structure, even when the telescope 13 is rotated about the optical axis L1, the camera head body 23 rotates about the optical axis L1, regardless of the operation of rotation of the telescope 13 about the optical axis L1, and the optical axis L2 of the image pickup optical system 25 is always positioned in the vertical direction.

Further, one end portion of a video signal line 34 is connected to the image pickup element 29. The video signal line 34 extends in a camera cable 35. The camera cable 35 is connected to a camera control unit 36. A TV monitor 37 is connected to the camera control unit 36. An output signal, which is sent from the image pickup element 29, is transmitted to the camera control unit 36 via the camera cable 35, and an endoscopic image is displayed on the TV monitor 37.

Figure 3B:
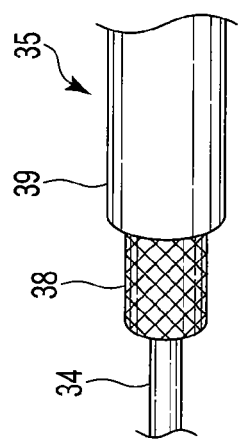
FIG. 3B is a perspective view showing the structure of a main part of a camera cable according to the first embodiment.

As shown in FIG. 3B, the camera cable 35 is configured such that the outer periphery of the video signal line 34 is covered with a net-like overall shield line 38. Further, the outer periphery of the overall shield line 38 is coated with an insulation coating film 39. Thus, the video signal line 34 is shielded by the overall shield line 38.

Further, in FIG. 1, the camera cable 35 is led out from a lower end portion of the camera head housing 24. A protection tube 40 is fitted on the led-out portion of the camera cable 35 at the lower end portion of the camera head housing 24.

A remote control section 41 is provided at a point along the camera cable 35 in the vicinity of the camera head body 23.

Specifically, the remote control section 41 is provided near the camera cable 35 so that the surgeon can easily operate the remote control section 41 by one hand, while holding the grip handle 15 of the telescope 13 by the other hand. Even if the remote control section 41 is moved by an operating force which is applied when the remote control section 41 is operated, this movement is absorbed by the camera cable 35 and is not transmitted to the camera head body 23.

FIG. 3A shows the internal structure of the remote control section 41. A remote control casing 41*a* is formed of a lightweight metal, such as aluminum, in a circular cylindrical shape. Opening portions 41*b* and 41*b* are provided at both ends of the remote control casing 41*a*. A shield cylinder body 42, which functions as a shield member and is formed of a lightweight metal, such as aluminum, in a circular cylindrical shape, is inserted in the remote control casing 41*a*.

A printed board 42*a* is fixed on an outer peripheral part of the shield cylinder body 42. A plurality of tact switches 43*a* are disposed at intervals on the printed board 42*a*. A plurality of push switches 44 are provided on the remote control casing 41*a* at positions opposed to the tact switches 43*a*. The push switches 44 are switch means which are operated by the finger of the surgeon.

A flange portion 45 and a positioning screw 46 are provided on an outer peripheral part of one end portion of the shield cylinder body 42. Further, a female screw portion 47 is provided on an inner peripheral part of the shield cylinder body 42 at one end portion of the shield cylinder body 42.

A camera cable 35 is inserted in the shield cylinder body 42. The overall shield line 38 and insulation coating film 39 of that part of the camera cable 35, which is covered with the shield cylinder body 42, are peeled off. In this peeled-off part, the video signal line 34 and operation signal line 48 are exposed. In the part other than the part that is covered with the shield cylinder body 42, the video signal line 34 and operation signal line 48 are covered with the overall shield line 38.

In addition, that part of the camera cable 35, which is covered with the shield cylinder body 42, is provided with a part where the overall shield line 38 and insulation coating film 39 are cut out. In this part, the video signal line 34 is passed through the shield cylinder body 42 in the axial direction. The operation signal line 48 is led out from a cut-out end portion 35*a* of the camera cable 35 into the shield cylinder body 42. A through-hole 44*a* is provided in an outer peripheral surface of one end portion of the shield cylinder body 42. The operation signal line 48 extends via the through-hole 44*a* of the shield cylinder body 42 to the outside of the shield cylinder body 42, and is connected by soldering to the printed board 42*a*.

Further, a cable fixing tube 49, which is engaged with the camera cable 35, is provided at one end portion (a left end portion in FIG. 3A) of the shield cylinder body 42. One end portion of the cable fixing tube 49 is provided with a male screw portion 50, and the other end portion of the cable fixing tube 49 is provided with an O ring 51 which is put in close contact with the camera cable 35.

An annular groove 52 is provided on an outer peripheral surface of an intermediate portion of the cable fixing tube 49. A fixing screw 53 is engaged by screwing in the cable fixing tube 49 in a diametrical direction. A calking tube 54, such as a ferrule, which is inserted the cable fixing tube 49, is fixed by the fixing screw 53.

The calking tube 54 has a circular cylindrical shape and is engaged with the cut-out end portion 35*a* of the camera cable 35. At the cut-out end portion 35*a* of the camera cable 35, the insulation coating film 39 is peeled off and the overall shield line 38 is exposed. The exposed overall shield line 38 is put in contact with the calking tube 54. The calking tube 54 is pressed on the overall shield line 38 by the fixing screw 53. Thereby, the calking tube 54 is connected to the overall shield line 38 in an electrically conductive state. The removal of the fixing screw 53 is prevented by a removal-prevention ring 55 which is engaged by screwing with the cable fixing tube 49.

A protection tube 56 is fitted over the cable fixing tube 49 and camera cable 35. A proximal end portion of the protection tube 56 is engaged with the annular groove 52 of the cable fixing tube 49.

A hold tube body 57 is engaged with an outer peripheral part of one end portion of the shield cylinder body 42. A proximal end portion of the hold tube 57 is provided with an engaging stepped portion 58 which engages the flange portion 45 of the shield cylinder body 42, and an O ring 59 which is put in close contact with an inner peripheral surface of the remote control casing 41*a*. A female screw portion 60 is formed on an inner peripheral surface of a distal end portion of the hold tube body 57. A male screw portion on an outer peripheral surface of a fastening ring 62 is screwed and fixed in the female screw portion 60. The inner peripheral surface of the fastening ring 62 includes a taper portion 61 for fastening the protection tube 56.

At the other end portion (a right end portion in FIG. 3A) of the shield cylinder body 42, a cable fixing tube 63 is integrally provided. The cable fixing tube 63 is formed substantially in the same fashion as the cable fixing tube 49 at the one end portion of the shield cylinder body 42. Specifically, a male screw portion 64 is provided on one end side of the cable fixing tube 63, and an O ring 65, which is put in close contact with the camera cable 35, is provided on the other end side of the cable fixing tube 63.

An annular groove 66 is provided on an outer peripheral surface of an intermediate portion of the cable fixing tube 63. Further, a fixing screw 67 is engaged by screwing in the cable fixing tube 63 in a diametrical direction. A calking tube 68, such as a ferrule, which is inserted the cable fixing tube 63, is fixed by the fixing screw 67.

The calking tube 68 has a circular cylindrical shape and is engaged with the cut-out end portion 35*a* of the camera cable 35. At the cut-out end portion 35*a* of the camera cable 35, the insulation coating film 39 is peeled off and the overall shield line 38 is exposed. The exposed overall shield line 38 is put in contact with the calking tube 68. The calking tube 68 is pressed on the overall shield line 38 by the fixing screw 67. The removal of the fixing screw 67 is prevented by a removal-prevention ring 69 which is engaged by screwing with the cable fixing tube 63.

Further, a protection tube 70 is fitted over the cable fixing tube 63 and camera cable 35. A proximal end portion of the protection tube 70 is engaged with the annular groove 66 of the cable fixing tube 63.

A female screw portion 71 is formed on an inner peripheral surface of the opening portion 41*c* of the remote control casing 41*a*. A male screw portion on an outer peripheral surface of a fastening ring 73 is screwed and fixed in the female screw portion 71. The inner peripheral surface of the fastening ring 73 includes a taper portion 72 for fastening the protection tube 70. The fastening ring 73 is provided with an O ring 74 which is put in close contact with an inner peripheral surface of the remote control casing 41*a*, and a flange portion 75 which abuts on an end face of the remote control casing 41*a*.

With the above-described structure, the following advantageous effects can be obtained. Specifically, in the present embodiment, the remote control section 41 is provided at a point along the camera cable 35 which is connected to the camera head body 23. Thus, the remote control section 41 functions as a balancer. Accordingly, even if the telescope 13 is rotated about its axis, smooth rotation at the annular groove 30 is enabled relative to the amount member 31. As a result, the camera head body 23 does not rotate together with the telescope 13, and the vertical attitude of the camera head body 23 can be kept.

Further, even if the remote control section 41 moves when the push switch 44 of the remote control section 41 is operated by the finger of the surgeon, the movement is absorbed by the camera cable 35. Therefore, the movement of the remote control section 41 is not transmitted to the telescope 13 and camera head body 23, and blurring of an image can be prevented when a still image is captured.

Although the remote control section 41 is provided at a point along the camera cable 35, the periphery of the video signal line 34 is covered with the shield cylinder body 42, and this is advantageous in EMC (electromagnetic compatibility). Further, the video signal line 34 penetrates the shield cylinder body 42 without intervention of a relay device such as a board. Therefore, the video signal does not deteriorate, and the impedance is not influenced. Besides, since there is no part of soldering for connecting lead wires, the number of fabrication steps can be reduced.

Moreover, since the camera head body 23 and remote control section 41 are separated, the camera head body 23 is reduced in size and weight, and the handling of camera head body 23 becomes easier.

Figure 4:
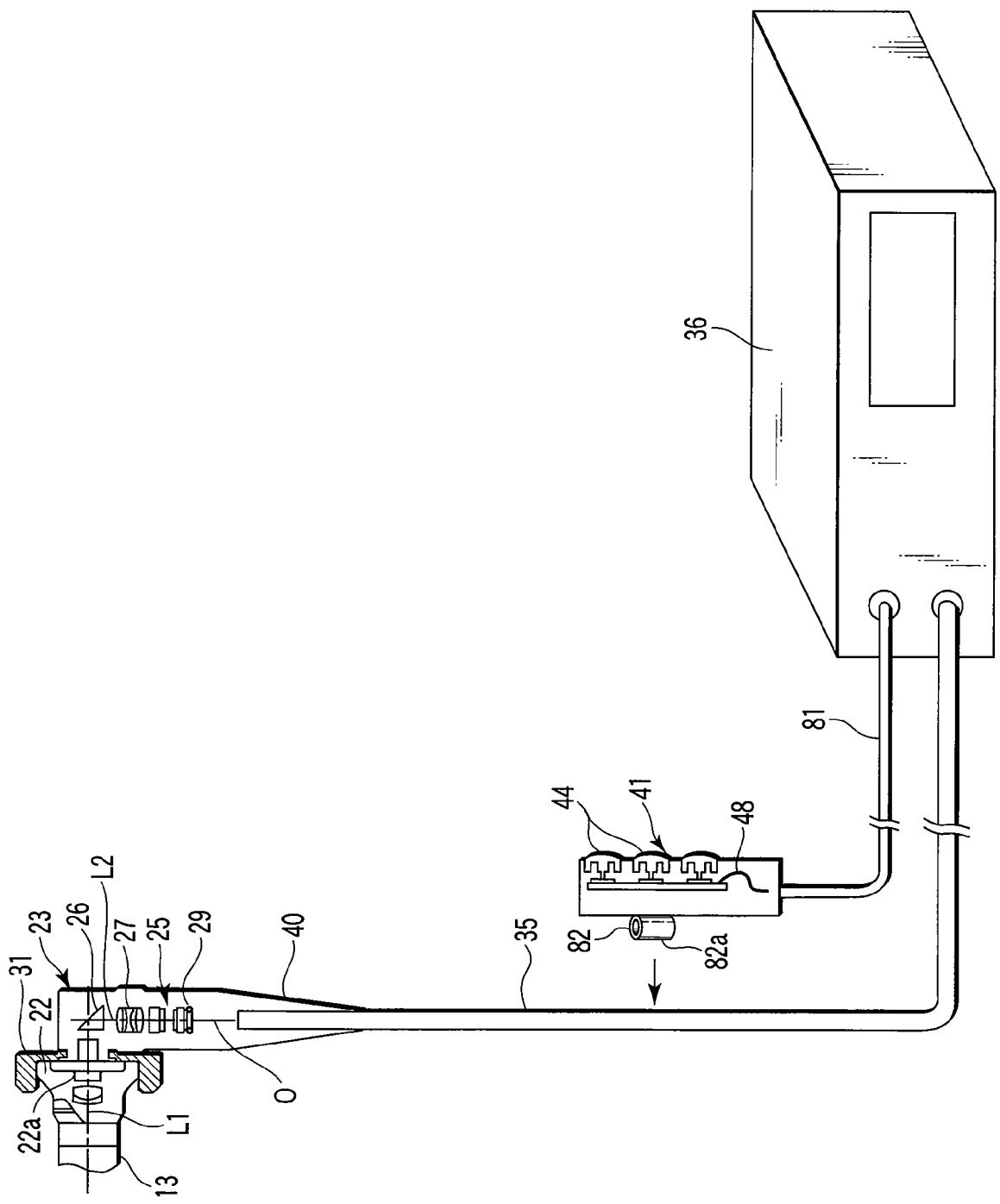
FIG. 4 shows the structure of an endoscopic image pickup device according to a second embodiment of the present invention.

FIG. 4 shows a second embodiment of the invention. In FIG. 4, the structural parts common to those in the first embodiment are denoted by like reference numerals, and a description thereof is omitted. The camera cable 35, which is led out from the camera head housing 24 of the camera head body 23 according to the present embodiment, is directly connected to the camera control unit 36.

A proximal end portion of a remote control cable 81 is connected to the camera control unit 36. A distal end portion of the remote control cable 81 is connected to a remote control section 41 which has basically the same structure as the remote control section 41 in the first embodiment. The remote control section 41 is provided with a clamp member 82 on a side thereof which is opposite to the push switches 44. The clamp member 82 is a tubular member which is formed of a synthetic resin or a rubber material, and is so shaped as to have a slit in a part thereof. The clamp member 82 can be fitted on an arbitrary part of the camera cable 35 by opening the part of the slit 82a. Thereby, the remote control section 41 can detachably be attached to the camera cable 35.

With the above-described structure, the following advantageous effects can be obtained. Specifically, in the present embodiment, the remote control section 41 can be supported at an arbitrary position, as desired by the surgeon, along the camera cable 35 which is connected to the camera head body 23. In addition, the remote control section 41 functions as a balancer. Accordingly, even if the telescope 13 is rotated about its axis, smooth rotation at the annular groove 30 is enabled relative to the amount member 31. As a result, the camera head body 23 does not rotate together with the telescope 13, and the vertical attitude of the camera head body 23 can be kept.

Further, even if the remote control section 41 moves when the push switch 44 of the remote control section 41 is operated by the finger of the surgeon, the movement is absorbed by the camera cable 35. Therefore, the movement of the remote control section 41 is not transmitted to the telescope 13 and camera head body 23, and blurring of an image can be prevented when a still image is captured.

Figure 5:
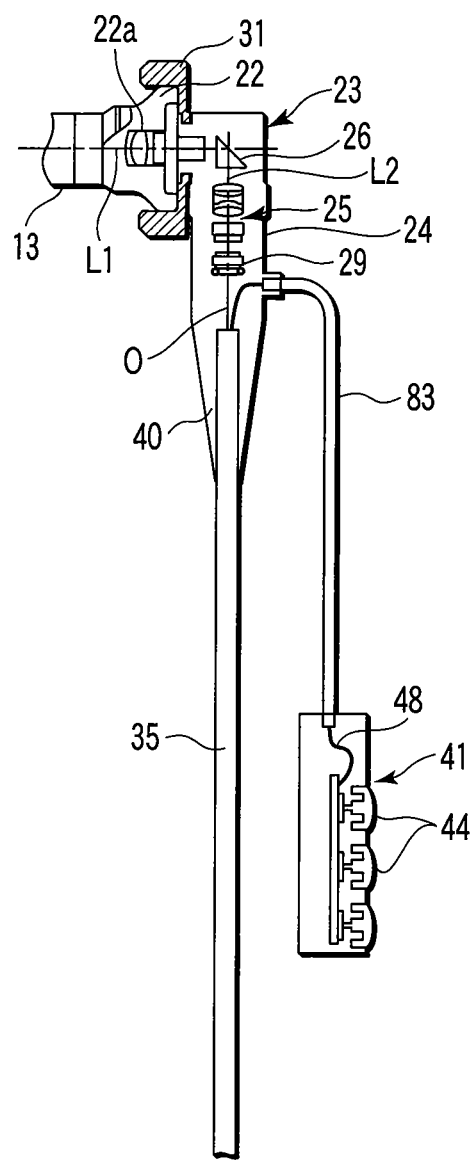
FIG. 5 shows the structure of an endoscopic image pickup device according to a third embodiment of the present invention.

FIG. 5 shows a third embodiment of the invention. In FIG. 5, the structural parts common to those in the first embodiment are denoted by like reference numerals, and a description thereof is omitted. In this embodiment, like the second embodiment, the camera cable 35, which is led out from the camera head housing 24 of the camera head body 23 according to the present embodiment, is directly connected to the camera control unit 36. In addition, a proximal end portion of a remote control cable 83 is connected to a side portion of the camera head housing 24. A distal end portion of the remote control cable 83 is connected to a remote control section 41 which has basically the same structure as the remote control sections 41 in the first and second embodiments.

With the above-described structure, the following advantageous effects can be obtained. Specifically, in the present embodiment, as regards the remote control section 41, the length of the remote control cable 83 which is connected to the camera head housing 24 can arbitrarily be set, as desired by the surgeon. In addition, the remote control section 41 functions as a balancer. Accordingly, even if the telescope 13 is rotated about its axis, smooth rotation at the annular groove 30 is enabled relative to the amount member 31. As a result, the camera head body 23 does not rotate together with the telescope 13, and the attitude of the camera head body 23 can be kept.

Further, even if the remote control section 41 moves when the push switch 44 of the remote control section 41 is operated by the finger of the surgeon, the movement is absorbed by the camera cable 83. Therefore, the movement of the remote control section 41 is not transmitted to the telescope 13 and camera head body 23, and blurring of an image can be prevented when a still image is captured.

In each of the above-described embodiments, the telescope has been described as the endoscope. Needless to say, the invention is also applicable to various rigid endoscopes and flexible endoscopes. The switches that are provided on the remote control section are not limited to push switches, and may be change-over switches, joystick-type switches or dial-type switches. Besides, the tact switches may be replaced with magnetic sensor type switches or photo-sensor type switches.

The present invention is not limited directly to the above-described embodiments. In practice, the structural elements can be modified and embodied without departing from the spirit of the invention. Various inventions can be made by properly combining the structural elements disclosed in the embodiments. For example, some structural elements may be omitted from all the structural elements disclosed in the embodiments. Furthermore, structural elements in different embodiments may properly be combined.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic image pickup device comprising:
    an insertion section which is configured to be inserted in a body cavity, and which includes a telescope having a first optical axis;
    a camera head body which includes an image pickup optical system having a second optical axis perpendicular to the first optical axis, and which is coupled to a proximal end portion of the insertion section, the camera head body being rotatable about the first optical axis, relative to the insertion section, and having a center of gravity offset from the first optical axis;

a camera cable, one end of which is connected to the camera head, and the other end of which is connected to the camera control unit, the camera control unit being configured to perform image processing based on an image picked up by the image pickup optical system; and a remote control section which is provided between the camera head body and the camera control unit in the camera cable in a state when the camera cable is connected to the camera control unit, and which includes a switch section configured to input an operation of the camera control unit by an operator, the remote control section being configured to function as a balancer to prevent the camera head body from rotating together with the telescope and to keep an attitude of the camera head body so that the camera body is extended from the proximal end portion of the insertion section toward a vertically down direction when the insertion section rotates about the first optical axis with respect to the camera head body, and movement of the remote control section being configured to be absorbed by the camera cable when the operation of the camera control unit is input in the switch section of the remote control section;

a video signal line which is extended from the image pick up optical system to the camera control unit through an inside of the camera cable and an inside of the remote control section, and which is configured to transmit a video signal from the image pickup optical system to the camera control unit based on the image picked up by the image pickup optical system; and a switch operation signal line which is extended from the switch section to the camera control unit through the inside of the camera cable, and is configured to transmit an operation final from the switch section to the camera control unit based on the operation input in the switch section of the remote control section.

2. The endoscopic image pickup device according to claim 1, wherein the camera cable is extended from the camera head body in a direction away from the telescope.

3. The endoscopic image pickup device according to claim 1, wherein the remote control section includes a shield member, which covers the video signal line and separates the switch section from the video signal line, wherein the video signal line is extended through an inside of the shield member.

4. The endoscopic image pickup device according to claim 3, wherein the camera cable includes a shield line which covers the video signal line and the switch operation signal line, and which is connected to the shield member of the remote control section.

* * * * *